United States Patent [19]

Adams et al.

[11] Patent Number: 4,876,374
[45] Date of Patent: Oct. 24, 1989

[54] PROCESS FOR MANUFACTURING AMIDES

[75] Inventors: Paul E. Adams; Darryl W. Kinzer, both of Willoughby Hills, Ohio

[73] Assignee: The Lubrizol Corporation, Wickliffe, Ohio

[21] Appl. No.: 54,172

[22] Filed: May 22, 1987

[51] Int. Cl.$^4$ .................................................. C07F 9/40
[52] U.S. Cl. .................................................. 558/109
[58] Field of Search .................................. 558/145, 109

[56] References Cited

U.S. PATENT DOCUMENTS

| | | | |
|---|---|---|---|
| 2,709,156 | 5/1955 | Bishop et al. | 558/109 |
| 2,901,481 | 8/1959 | Fusco et al. | 260/268 |
| 3,238,202 | 3/1966 | Peri et al. | 260/247.1 |
| 3,265,773 | 8/1966 | Losco et al. | 260/943 |
| 3,845,171 | 10/1974 | Beriger | 260/943 |
| 3,933,659 | 1/1976 | Lyle et al. | 252/32.7 |
| 3,933,945 | 1/1976 | Beriger | 260/943 |
| 3,991,140 | 11/1976 | Beriger | 260/940 |
| 4,032,461 | 6/1977 | Hoke | 252/46.7 |
| 4,162,279 | 7/1979 | Walsh et al. | 260/943 |
| 4,175,043 | 11/1979 | Harodysky | 252/32.7 |
| 4,177,300 | 12/1979 | Walsh et al. | 427/390 |
| 4,208,357 | 6/1980 | Hoke | 260/978 |
| 4,282,171 | 8/1981 | Hoke | 260/928 |

FOREIGN PATENT DOCUMENTS 517089  10/1955  Canada ................................ 558/170

OTHER PUBLICATIONS

Wolf et al., Deutsche Lebensmittel-Rundschau, vol. 64(6), pp. 171-177, German-English Translation of Wolf et al., No. 860718, Jul. 1986, pp. 1-8.

Primary Examiner—Anton H. Sutto
Attorney, Agent, or Firm—Robert A. Franks; Frederick D. Hunter; Forrest L. Collins

[57] ABSTRACT

Amide compounds useful as additives in lubricating fluids as extreme pressure/antiwear agents are produced on a manufacturing scale. The amides are produced by simultaneously adding together and reacting a phosphorus-containing acid and aqueous acrylamide. Substantially equal molar amounts of the phosphorus-containing acid and the aqueous acrylamide are added together with sufficient cooling to maintain the reaction at a temperature below 50° C. After insolation, the reaction product obtained is preferably further reacted with a coupling agent, preferably paraformaldehyde.

9 Claims, No Drawings

PROCESS FOR MANUFACTURING AMIDES

CROSS REFERENCE

This application claims subject matter related to the disclosure of pending U.S. application Ser. No. 853,485 filed April 18, 1986 which was a continuation-in-part of pending application Ser. No. 730,877 filed May 3, 1985. Both applications being co-invented by a coinventor named herein. Both of the earlier applications are incorporated herein by reference in their entirety and priority by both earlier applications is claimed to the extent possible under 35 USC Section 120.

FIELD OF THE INVENTION

The present invention relates to the field of chemical synthesis of amide compounds. More specifically, the present invention relates to a unique process for simultaneously combining and reacting together a phosphorus-containing acid, and an aqueous acrylamide in order to form an amide useful as an intermediate and as an additive in lubricating fluids as an extreme pressure/antiwear agent. The reaction product obtained by reacting the phosphorus containing acid, and aqueous acrylamide is isolated and preferably further reacted with a coupling agent, preferably paraformaldehyde in order to form a bis-amide product which is useful as an extreme pressure/antiwear agent in lubricating fluids.

BACKGROUND OF THE INVENTION

A number of different types of phosphorus and sulfur containing amides and thioamide compounds useful as lubricant additives are disclosed in U.S. Pat. Nos. 4,282,171; 4,208,357; and 4,032,461 all to Hoke. These patents also disclose processes for producing such compounds and lubricating compositions containing them.

U.S. Pat. No. 4,175,043 to Horodysky discloses a product formed by forming the metal salt of the product of reaction between a dialkyl or diaryl phosphorodithioic acid and a sulfurized olefin. This reaction product is indicated as having good antiwear and antioxidant activity.

U.S. Pat. No. 3,933,659 to Lyle discloses a functional fluid comprised of a major amount of an oil of lubricating viscosity and an effective amount of a number of additive components including a dihydrocarbyl dithiophosphoric acid.

These patents discussed above are alike in that they are primarily directed toward compounds useful as lubricant additives and various lubricating compositions containing such additives. These patents do however also discuss the insecticidal and pesticidal properties of some of these compounds as well as processes for preparation. Other publications referred to below are alike in that they are primarily directed toward compounds useful as insecticides and pesticide which compounds are generally not oil soluble.

U.S. Pat. No. 2,901,481 to Fusco et al discloses processes for preparing insecticides in the form of dialkyldithiophosphoric acid ester derivatives having two acid groups in the molecule.

U.S. Pat. Nos. 3,238,202 to Peri et al; 3,265,773 to Losco et al; and 3,845,171; 3,933,945; and 3,991,140 all to Beriger disclose various pesticidal compounds in the form of amide derivatives of different dialkyldithiophosphoric acid components.

Similar insecticides and processes for producing them are disclosed in Wolf et al. Deutsche Lebensmittel - Rundschau, Vol 64 (6) pp. 171–177, (1968). Related compounds in the form of phosphoroxycarboxamides useful as flame retardants are discloses in U.S. Pat. Nos. 4,162,279 and 4,177,300 both to Walsh et al.

The present invention is directed toward processes for efficiently and economically producing a wide range of amine derivatives of dialkyldithiophosphoric acids which might be useful in a number of ways including, lubricant and fuel additives, pesticides, insecticides, and flame retardants. By improving the ease and efficiency by which a large group of compounds can be prepared and decreasing the cost of production, it is hoped that such a compound can be made more readily available.

SUMMARY OF THE INVENTION

In accordance with the present invention a variety of different kinds of amide compounds are produced by a particular process and such compounds are added to oils of lubricating viscosity in order to improve the extreme pressure/antiwear properties of the oils. The specific process involves the simultaneous addition and reacting of a phosphorus-containing acid and aqueous acrylamide. The phosphorus-containing acid and aqueous acrylamide are concomitantly combined in substantially equal molar amounts while maintaining sufficient cooling to keep the reaction temperature below 50° C. The simultaneous addition of the two components while maintaining the temperature at the low level allows for the reaction to take place in the desired manner. After the reaction is completed the reaction product is isolated by removing water and alcohols. The isolated product is further reacted with formaldehyde in order to form a bis-amide product. The bis-amide product may be isolated.

A primary object of the invention is to provide an improved process for forming amide compounds.

An advantage of the present invention is that the process reduces intermediate and final product amide hydrolysis.

A feature of the present invention is that the products resulting from the process are less dark and less odorous and produced in a higher yield.

Another advantage of the present invention is that the process reduces the amount of acrylamide homopolymerization thus increasing the degree of coupling which takes place.

Yet another advantage of the present invention is that it results in a product having increased thermal stability.

These and other objects, advantages and features of the present invention will become apparent to those persons skilled in the art upon reading the details of the structure, synthesis and usage as more fully set forth below. Reference being made to the accompanying general structural formula forming a part hereof wherein like symbols refer to like molecular moieties throughout.

DETAILED DESCRIPTION OF THE INVENTION

Before the present process for manufacturing an amide is described, it is to be understood that this invention is not limited to the particular reactants and reaction conditions described as such may, of course, vary. It is also understood that the terminology used herein is for the purpose of describing particular embodiments only, and is not intended to be limiting since the scope of the present invention will be limited only by the appended claims.

It must be noted that as used in this specification and the appended claims, the singular forms "a" and "an" and "the" include plural referents unless the context clearly dictates otherwise. Thus, for example, reference to a "phosphorus containing acid" includes mixtures of such phosphorus-containing acids, reference to "an aqueous acrylamide" includes various aqueous acrylamide compositions, other amides such as methacrylamide, crotonamide and so forth.

The present invention is a process for reacting an aqueous form of acrylamide and a phosphorus-containing acid in order to form an amide compound. The acrylamide compounds useful in connection with the present invention have the following general structural formula:

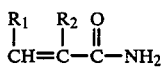   (I)

wherein $R_1$ and $R_2$ are independently hydrogen or hydrocarbyl and are preferably hydrogen or methyl, more preferably hydrogen.

The phosphorus-containing acid component has the following general structural formula:

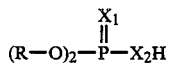   (II)

wherein R is hydrocarbyl and is preferably an alkyl group containing 1 to 24 carbon atoms and $X_1$ and $X_2$ are independently sulfur or oxygen, more preferably sulfur.

When the aqueous acrylamide (I) is reacted with the phosphorus-containing acid (II) an amide having the following general structural formula is produced:

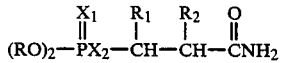   (III)

wherein R, $R_1$ and $R_2$ are each independently hydrogen or hydrocarbyl but R is preferably an alkyl group containing 1 to 24 carbon atoms and $R_1$ and $R_2$ are preferably hydrogen or methyl, more preferably hydrogen and $X_1$ and $X_2$ are independently sulfur or oxygen but are preferably sulfur.

As used herein, the term "hydrocarbyl" denotes a radical having a carbon atom directly attached to the remainder of the molecule and having predominantly hydrocarbon character within the context of this invention. Such radicals include the following:

(1) Hydrocarbon radicals; that is, aliphatic, (e.g., alkyl or alkenyl), alicyclic (e.g., cycloalkyl or cycloalkenyl), aromatic, aliphatic and alicyclic-substituted aromatic, aromatic-substituted aliphatic and alicyclic radicals, and the like, as well as cyclic radicals wherein the ring is completed through another portion of the molecule (that is, any two indicated substituents may together from an alicyclic radical). Such radicals are known to those skilled in the art; examples are (2) Substituted hydrocarbon radicals; that is, radicals containing non-hydrocarbon substituents which, in the context of this invention, do not alter the predominantly hydrocarbon character of the radical. Those skilled in the art will be aware of suitable substituents; examples are (3) Hetero radicals; that is, radicals which, while predominantly hydrocarbon in character within the context of this invention, contain atoms other than carbon present in a chain or ring otherwise composed of carbon atoms. Suitable hetero atoms will be apparent to those skilled in the art and include, for example, nitrogen, oxygen and sulfur.

In general, no more than about three substituents or hetero atoms, and preferably no more than one, will be present for each 10 carbon atoms in the hydrocarbyl radical.

Terms such as "alkyl-based radical", "aryl-based radical" and the like have meaning analogous to the above with respect to alkyl and aryl radicals and the like.

Preferably, the hydrocarbyl radicals in the compounds of this invention are free from acetylenic and usually also from ethylenic unsaturation and have about at least one carbon atom. The radicals are usually hydrocarbon and especially lower hydrocarbon, the word "lower" denoting radicals containing up to seven carbon atoms. They are preferably lower alkyl or aryl radicals, most often alkyl.

The present inventors have found that it was somewhat difficult to react the aqueous acrylamide (I) with the phosphorus-containing acid component (II) in order to obtain the desired reaction product (III). Environmental safety and cost constraints make it necessary to utilize the acrylamide in an aqueous form. When used in this form it is possible to add the aqueous acrylamide to the acid. However, the inventors found that such an addition provides for substantial raw material and intermediate amide hydrolysis. The resulting product is dark, odorous and relatively low in yield as compared with the expected yield based on the molar amounts of the starting material. Further, the product has reduced stability and forms haze after filtration when isolation is attempted.

The present inventors then tried carrying out the reverse reaction. More specifically, the phosphorus-containing acid component was added to the aqueous acrylamide under manufacturing conditions. This process resulted in homopolymerization of the acrylamide. The same reaction was attempted in the presence of polymerization inhibitors. However, polymerization still occurred in an unacceptable amount resulting in production down time, high costs and a relatively low yield based on the molar amounts of the starting material.

The present inventors have found that it is possible to greatly improve the desired results and obtain a relatively high yield with respect to the amount of compound (III) obtained by simultaneously adding together and reacting the aqueous acrylamide (I) and the phosphorus-containing acid component (II). Further, the present inventors found that it is preferable to simultaneously add these two components together into a vessel which includes a neutral intermediate amide heel, i.e. an amount of the desired product (III). The amount of the amide heel can be adjusted by those skilled in the art to obtain optimal results. It has been found that it is desirable to carry out the reaction in a vessel having a rotating agitator blade mounted on the bottom of the vessel and that the amide heel be added initially in an amount sufficient to cover the agitator blade.

When the process is carried out by simultaneously adding the two components to the neutral intermediate amide heel, the result is a minimization of the hydrolysis while preventing acrylamide homopolymerization.

Further, when this procedure is combined with other refinements such as sequential water strips and reduced temperature during filtration the resulting product is produced in a relatively high yield, is clear and relatively stable with an agreeable odor.

Although it is possible to combine the reactants in various amounts and obtain acceptable results, the present inventors have found that it is desirable to add the aqueous acrylamide (I) and phosphorus-containing acid components (II) such that substantially equal molar amounts of (I) and (II) are reacted together. Accordingly, it is preferable if (I) and (II) are combined together in a reaction vessel at rates such that the molar amounts of acrylamide: phosphorus-containing acid are (1:1). However, some variation in the molar ratio may be allowed, e.g. (0.9–1.10):(0.9–1.10), with a ratio of (0.95–1.05):(0.95–1.05) being more preferred. In general, the closer the ratio is to (1:1) the better the results.

Further, although the temperature of reaction can vary over a wide range the present inventors have found that it is desirable to cool the reaction in order to maintain a temperature below 65° C. and more preferably between 40° C. and 50° C. When the reaction is completed the reaction products will include a relatively high yield of the reaction component (III) along with some water and alcohols.

The aqueous acrylamide (I) and phosphorus-containing acid (II) reactants may be combined together in a variety of different ways. For example, the reactants may be simultaneously added to a vessel in substantially equal molar amounts. It is important that the reactants be concomitantly combined together in substantially stoichiometrically equal amounts. If too much of the aqueous acrylamide is added too quickly, undesirable homopolymerization takes place in the environment of excess acrylamide. If too much phosphorus-containing acid is added too quickly undesirable hydrolysis takes place. Thus the invention involves combining the reactants together at such a rate that undesired homopolymerization and hydrolysis are reduced to a minimum and the yield of the final product is increased to a maximum. Such results can be obtained by simultaneously bringing into contact stoichiometrically equal amounts of the reactants. The reactants might be brought into contact by adding them to a vessel or by causing them to flow or be sprayed toward each other from separate supply lines.

The water and alcohol contaminants are removed from the desired amide product of formula (III). The isolated product is then subject to a coupling reaction by reacting the amide (III) with a coupling agent, preferably paraformaldehyde in order to form a bis-amide having the following general structural formula:

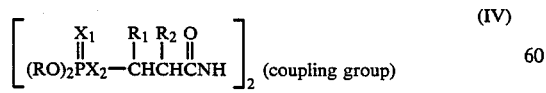
(IV)

wherein R, $R_1$ and $R_2$ are each independently hydrogen or hydrocarbyl and $X_1$ and $X_2$ are independently sulfur or oxygen and the "coupling group" is represented by structural formula (V) shown below. R is preferably an alkyl containing 1 to 24 carbon atoms, more preferably 6-18 carbon atoms, $R_1$ and $R_2$ are preferably hydrogen or methyl, more preferably hydrogen, X is preferably sulfur, and the "coupling group" is preferably —$CH_2$—.

The bis-amide compounds of formula (IV) are formed by reacting the amide compounds of formula (III) with a coupling agent in the form of an aldehyde or ketone (or a reaction synthon equivalent of an aldehyde or ketone) of the following formula:

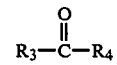

wherein $R_3$ and $R_4$ are independently an alkyl moiety having from 1 to 12 carbon atoms, a phenyl moiety, or an alkyl substituted phenyl moiety having from 7 to 12 carbon atoms and one of $R_3$ or $R_4$ may be hydrogen. The coupling agent is preferably formaldehyde, more preferably paraformaldehyde which can result in methylene and di-methylene ether coupling groups. The coupling agents form a coupling group of formula (V):

wherein $R_3$ and $R_4$ are defined as above.

The coupling reaction desirably takes place in the presence of strong mineral or organic acids such as HCl, $H_2SO_4$, $H_3PO_4$, $CH_3SO_3H$, p-toluenesulfonic acid, and the like. The amount of the acid catalyst is generally from about 0.3 to about 1.5% by weight, desirably from about 0.8 to about 1.2%, and preferably from about 0.9 to about 1.1% by weight based upon the weight of the total product formed. Although lesser amounts of catalyst can be utilized, the reaction is generally slower and a smaller fraction of the desired product is formed. The reaction with the coupling agent initially takes place at a temperature of from about 80° C. to about 120° C. and desirably from about 80° C. to about 100° C. in an inert atmosphere. The final reaction temperature is generally higher as from about 80° C. to about 110° C. and desirably from about 90° C. to about 100° C.

The amount of reaction product (III) reacted with the coupling agent is from about 0.3 to about 3.0 weight equivalents utilized per weight equivalent of said coupling agent with a 1:1 equivalent ratio being preferred. The coupling agent may be a mixture of different coupling agents and preferably includes paraformaldehyde.

The combination of formaldehyde and phosphorus containing amide compound (III) as described above may couple two amides or may result in the formation of a —$CH_2OH$ on the nitrogen atom of the amide. Two of such amides with a —$CH_2OH$ group thereon may then be reacted to form a coupled amide with the coupling group being

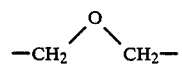

Uncoupled compounds may be used in a lubricant and when used a coupling reaction may take place during use and this may be beneficial to the load-carrying lubricating properties of the overall oil composition.

As briefly discussed above, the compounds of the present invention are particularly useful as additives for lubricating compositions. The compounds of the present invention are particularly useful as additives for lubrication where they function primarily as load-carrying agents, high or extreme pressure anti-wear agents, oxidation inhibitors, corrosion-inhibitors, and the like. Lubricating compositions containing the compounds of the present invention as additives comprise a major proportion of a lubricating oil and a minor portion of said compound sufficient to improve the load-carrying ability, anti-wear ability, oxidation-inhibitor or corrosion-inhibiting properties of the composition.

In general, the compounds of formula (III) or (IV) alone or in combinations are used in lubricants in an amount of from about 0.01 to about 5% by weight and desirably from about 0.1 to about 1% by weight based on total weight of the lubricating composition. Additionally, the compounds of the present invention can be utilized in a concentration form or a lubricant concentrate in an amount of from about 0.5 to about 50% by weight and more desirably from about 1 to about 25% by weight based upon the total weight of the concentrate package. In addition to the compounds of the present invention, the concentrate package can contain one or more compounds such as anti-wear agents, load-carrying agents, corrosion-inhibitors, oxidation inhibitors, demulsifiers, foam inhibitors, VI improvers, pour point depressants, detergents, dispersants, and the like. The compounds of the present invention can also be used as insecticides or pesticides.

Various couplers may be used to provide a variety of different types of coupled phosphorus-containing amides. Other reactions attach other functional groups to the phosphorus-containing amides of formula (III). These uncoupled compounds may be present in a mixture with various bis-amides (e.g. paraformaldehyde coupled i.e. methylene linked amides) in a lubricant oil which is useful in providing the desirable properties or load-carrying agents, extreme pressure agents, and generally as additives in lubricating compositions.

The process steps of the present invention are preferably fashioned so as to provide a statistical mixture (i.e., coupled and uncoupled compounds each with different substituent groups providing a variety of different compounds) of different phosphorus containing amide compounds bonded to or coupled by different coupling groups. Any such statistical mixture is produced by the processes described herein is likely to include some methylene coupled amide compounds. When the coupling group is methylene the R groups on the phosphorus containing acid generally must contain more than 6 carbon atoms in order to maintain good oil solubility. However, the groups are generally methyl if the resulting compound is to be an insecticide. Although the "coupling group" is preferably methylene it can be selected from the group consisting of:

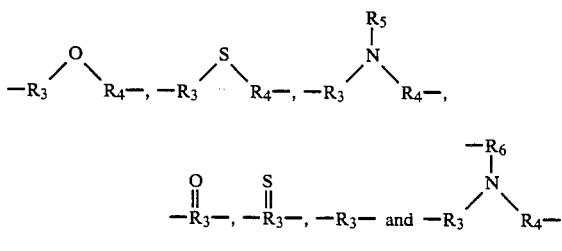

wherein $R_3$ and $R_4$ are defined as above but can not be hydrogen and $R_6$ is defined the same as $R_3$ and $R_4$ and $R_5$ is the same as $R_6$ but can be hydrogen.

When the coupled bis-amide product is added to an oil of lubricating viscosity such as an oil generally used in connection with hydraulic fluids, the bis-amide product greatly improves the extreme pressure and antiwear characteristics of the fluid. Those skilled in the art will vary the amount of coupled bis-amide added to the oil in order to obtain optimal results.

In general the coupled bis-amide may be added to an oil of lubricating viscosity, (e.g. bright stock) in an amount in the range of from about 0.005 to 5.0%, preferably from about 0.05 to 3.0% and more preferably about 0.1 to 1.0%.

The following examples are provided so as to provide those of ordinary skill in the art with a complete disclosure and description of how to carry out the processes and produce the compounds of the invention and are not intended to limit the scope of what the inventors regard as their invention. Efforts have been made to ensure accuracy with respect to numbers used (e.g., amounts, temperature, etc.) but some experimental errors and deviation should be accounted for. Unless indicated otherwise, parts of parts by weight, temperature is in degrees centigrade and pressure is at or near atmospheric.

EXAMPLE 1

Prepare an amide heel within a suitable reactor vessel having an agitator blade at its bottom by combining 961 lbs (2.29 equivalents) of O,O-di-isooctyl phosphorodithioic acid with 325 lbs (2.29 equivalents) of 50% aqueous acrylamide. The combined acid and acrylamide are continually mixed with the agitator blade of the reactor vessel while maintaining the temperature of the reactants below 50° C. Allow the reaction to continue to completion forming an amide heel of sufficient volume to cover the agitator blades of the reactor vessel. Then add 3757 lbs (8.95 equivalents) of O-O-di-isooctyl phosphorodithioic acid and 1271 lbs (8.95 equivalents) of acrylamide solution, the acid and acrylamide being added simultaneously at substantially the same rate over a six hour period while continuing the movement of the agitator blades of the vessel. Continue cooling the reaction during the addition of the acid and acrylamide to maintain the reactor temperature below 50° C. Apply a vacuum (90 mm Hg absolute) in order to remove isooctyl alcohol and water while heating the reactor vessel to about 70° C. After reaching a temperature of about 70° C., add 217 lbs (6.57 equivalents) of paraformaldehyde and 40 lbs (0.29 equivalents) of methane sulfonic acid. Raise the temperature of the reaction mixture to about 85°–90° C. while continuing to agitate the reactants within the vessel. Continue the reaction for about 2 hours and them apply a vacuum (50 mm Hg absolute) and remove water at a temperature in the range of about 85°–90° C. Continue the temperature in the range of 85°–90° C. for a 3 hour period while continuing to remove water under vacuum and complete the stripping. Neutralize the acid catalyst with about 11.3 lbs (0.30 equivalents) of lime. After neutralization, remove the water of neutralization at 85°–90° C. under a vacuum of about 50 mm Hg absolute. Filter the mixture obtained through a filter aid and obtain the filtrate which is the desired coupled amide product. The product should contain 6.64% phosphorus (6.67% theoretical) and about 2.67% nitrogen (2.82% theoretical).

EXAMPLE 2

Prepare an amide heel in the manner described in Example 1. The heel should be of sufficient volume to cover the agitator blades of the reactor vessel. Then add (10.0 molar equivalents) of O-O-di-isodecyl phosphorodithioic acid and (10.0 molar equivalents) of acrylamide solution, the acid and acrylamide being added concomitantly at substantially stoichiometrically equal amounts while continuing the movement of the agitator blades of the vessel. Continue cooling the reaction during the addition of the acid and acrylamide to maintain the reactor temperature below 65° C. Apply a vacuum in order to remove alcohols and water while heating the reactor vessel. After reaching a temperature of about 70° C, add (5.0 molar equivalents) of formaldehyde and a catalytic amount of methane sulfonic acid. Raise the temperature of the reaction mixture to about 85°–90° C. while continuing to agitate the reactants within the vessel. Continue the reaction to completion and then apply a vacuum and remove water at a temperature in the range of about 85°–90° C. Continue the temperature in the range of 85°–90° C. while continuing to remove water under vacuum and complete the stripping. Neutralize the acid catalyst with lime. After neutralization, remove the water of neutralization at 85°–90° C. under a vacuum. Filter the mixture obtained through a filter aid and obtain the filtrate which is the desired bis-amide product.

EXAMPLE 3

Prepare an amide heel within a suitable reactor vessel having an agitator blade at its bottom by combining (about 10 molar equivalents) of O,O-di-methyl phosphorodithioic acid with 50% aqueous acrylamide (10 molar equivalents of acrylamide). The combined acid and acrylamide are continually mixed with the agitator blade of the reactor vessel while maintaining the temperature of the reactants below 50° C. Allow the reaction to continue to completion forming an amide heel of sufficient volume to cover the agitator blades of the reactor vessel. Then add about (100 molar equivalents) of O-O-di-methyl phosphorodithioic acid and (about 100 molar equivalents) of acrylamide solution, the acid and acrylamide being added simultaneously at substantially the same rate to avoid adding an excess of one reactant over the other while continuing the movement of the agitator blades of the vessel. Continue cooling the reaction during the addition of the acid and acrylamide to maintain the reactor temperature below 50° C. Apply a vacuum in order to remove alcohols and water while heating the reactor vessel to about 70° C. After reaching a temperature of about 70° C., add (60 molar equivalents) of paraformaldehyde. Raise the temperature of the reaction mixture to about 85°–90° C. while continuing to agitate the reactants within the vessel. Continue the reaction then apply a vacuum and remove water at a temperature in the range of about 85°–90° C. Continue the temperature in the range of 85°–90° C. while continuing to remove water under vacuum and complete the stripping. Neutralize the acid catalyst with lime. After neutralization, remove the water of neutralization at 85°–90° C. under a vacuum. Filter the mixture obtained through a filter aid and obtain the filtrate which is the desired coupled amide product useful as a pesticide.

EXAMPLE 4

Prepare a mixture of phosphorodithioic acids of general structural formula (II) wherein R is an alkyl moiety and the mixture provides a statistical average for R at about 8 carbon atoms. Concomitantly combine the acid mixture with substantially stoichoimetrically equal molar amounts of acrylamide while continually providing agitation and maintaining the temperature below about 65° C. Continue mixing and maintaining the temperature below 65° C. until the reaction is complete. Raise the temperature to about 70° C. and apply vacuum to remove water and alcohols. When water and alcohols are no longer being drawn off, add paraformladehyde in a molar amount sufficient to from a bis-amide with substantially all of the amide reaction product formed in the first reaction. Raise the temperature to around 80° to 95° C. and maintain until the reaction is complete. Apply a vacuum while maintaining elevated temperature until stripping is completed. Filter the resulting mixture to obtain the bis-amide filtrate product.

EXAMPLE 5

Prepare a mixture of phosphorodithioic acids of general structural formula (II) wherein R is an alkyl moiety and the mixture provides a statistical average for R at about 12 carbon atoms. Concomitantly combine the acid mixture with substantially stoichoimetrically equal molar amounts of a mixture of acrylamides of formula (I) while continually providing agitation and maintaining the temperature below about 55° C. Continue mixing and maintaining the temperature below 55° C. until the reaction is complete. Raise the temperature to about 70° C. and apply vacuum to remove water and alcohols. When water and alcohols are no longer being drawn off, add a mixture of coupling agents in a molar amount sufficient to from a bis-amide of formula (IV) with substantially all of the amide reaction product formed in the first reaction. Raise the temperature to around 80° to 95° C. and maintain until the reaction is complete. Apply a vacuum while maintaining elevated temperature until stripping is completed. Filter the resulting mixture to obtain a statistical mixture of bis-amide filtrate product of general formula (IV).

EXAMPLE 6

Prepare a mixture of phosphorodithioic acids of general structural formula (I) wherein R is an alkyl moiety and the mixture provides a statistical average for R at about 8 carbon atoms. Simultaneously combine the acid mixture with substantially stoichoimetrically equal molar amounts of acrylaxide while continually providing agitation and maintaining the temperature below about 50° C. Continue mixing and maintaining the temperature below 65° C. until the reaction is complete. Raise the temperature to about 70° C. and apply vacuum to remove water and alcohols. Apply a vacuum while maintaining elevated temperature until stripping is completed. Filter the resulting mixture to obtain a mixture of amide filtrate product.

EXAMPLE 7

Prepare a mixture of phosphorodithioic acids of general structural formula (I) wherein R is independently two different alkyl moieties containing 8 and 12 carbon atoms. Concomitantly combine the acid mixture with substantially stoichometrically equal molar amounts of acrylamide while continually providing agitation and maintaining the temperature below about 60° C. Continue mixing and maintaining the temperature below 60° C. until the reaction is complete. Raise the temperature to about 70° C. and apply vacuum to remove water and alcohols. When water and alcohols are no longer being drawn off, add paraformladehyde in a molar amount sufficient to form a bis-amide with substantially all of the amide reaction product formed in the first reaction. Raise the temperature to around 80° to 95° C. and maintain until the reaction is complete. Apply a vacuum while maintaining elevated temperature until stripping is completed. Filter the resulting mixture to obtain the bis-amide filtrate product.

The instant invention is shown and described herein in what is considered to be the most practical, and preferred, embodiments. It is recognized, however, that departures may be made therefrom which are within the scope of the invention, and that obvious modifications will occur to one skilled in the art upon reading this disclosure.

We claim:

1. A process for producing amide compounds comprising the steps of:

reacting an aqueous acrylamide (I) and a phosphorus-containing acid having the following general structural formula: (II)

wherein R is hydrocarbyl and $X_1$ and $X_2$ are independently selected from the group consisting of sulfur and oxygen, the reacting being carried out by concomitantly combining substantially stoichometrically equal amounts of acrylamide present in the aqueous acrylamide (I) and phosphorus-containing acid (II); and obtaining a reaction product in the form of an amide having the following general structural formula: (III)

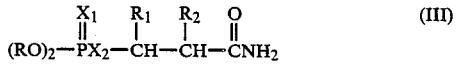

wherein R is hydrocarbyl, $R_1$ and $R_2$ are independently hydrogen or methyl and $X_1$ and $X_2$ are independently selected from the group consisting of sulfur and oxygen.

2. The process as claimed in claim 1, wherein the aqueous acrylamide and phosphorus-containing acid are reacted while maintaining a temperature below 65° C.

3. The process as claimed in claim 1, wherein R is an alkyl moiety containing about 1 to about 24 carbon atoms and $X_1$ and $X_2$ are sulfur.

4. The process as claimed in claim 1, wherein the aqueous acrylamide and phosphorus-containing acid components are simultaneously combined in substantially equal molar amounts.

5. The process as claimed in claim 1, wherein the aqueous acrylamide and phosphorus containing acid components are combined together in a vessel containing an amide heel having the following general structural formula: (III)

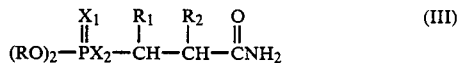

wherein R is hydrocarbyl, $R_1$ and $R_2$ are independently hydrogen or methyl and $X_1$ and $X_2$ are independently selected from the group consisting of sulfur and oxygen.

6. A process for producing amide compounds comprising the steps of:

reacting an aqueous acrylamide (I) and a phosphorus-containing acid having the following general structural formula: (II)

wherein R is hydrocarbyl and $X_1$ and $X_2$ are independently selected from the group consisting of sulfur and oxygen, the reacting being carried out by simultaneously adding to a vessel substantially equal molar amounts of acrylamide present in the aqueous acrylamide (I) and phosphorus-containing acid (II); and obtaining a reacation product in the form of an amide having the following general structural formula: (III)

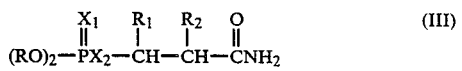

wherein R is hydrocarbyl, $R_1$ and $R_2$ are independently hydrogen or methyl and $X_1$ and $X_2$ are independently selected from the group consisting of sulfur and oxygen.

7. The process as claimed in claim 6, wherein the aqueous acrylamide and phosphorus-containing acid are reacted while maintaining a temperature below 65° C., under vacuum while continually drawing off water of vaporization.

8. The process as claimed in claim 6, wherein R is an alkyl moiety containing about 1 to about 24 carbon atoms, $X_1$ and $X_2$ are sulfur, and $R_1$ and $R_2$ are each hydrogen.

9. The process as claimed in claim 1, wherein the aqueous acrylamide and phosphorus containing acid components are added to a vessel containing an amide heel having the following general structural formula: (III)

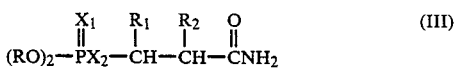

wherein R is hydrocarbyl, $R_1$ and $R_2$ are independently hydrogen or methyl and $X_1$ and $X_2$ are independently selected from the group consisting of sulfur and oxygen.

* * * * *